(12) United States Patent
Yang et al.

(10) Patent No.: US 9,044,501 B2
(45) Date of Patent: Jun. 2, 2015

(54) **METHOD OF PREVENTING AND/OR TREATING A NEURODEGENERATIVE DISEASE BY ADMINISTERING AN EXTRACT OF *LYCORIS CHEJUENSIS* AND/OR A COMPOUND ISOLATED THEREFROM**

(75) Inventors: Hyun-Ok Yang, Gangneung-si (KR); Hak-Cheol Kwon, Seoul (KR); Jin-Soo Park, Gangneung-si (KR); Sung-Kwon Chung, Seoul (KR); Myung-Soo Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 1120 days.

(21) Appl. No.: 12/607,972

(22) Filed: Oct. 28, 2009

(65) Prior Publication Data

US 2010/0227851 A1 Sep. 9, 2010

(30) Foreign Application Priority Data

Mar. 4, 2009 (KR) .......................... 10-2009-0018520

(51) Int. Cl.
*A61K 36/896* (2006.01)
*A61K 31/4741* (2006.01)

(52) U.S. Cl.
CPC ........... *A61K 36/896* (2013.01); *A61K 31/4741* (2013.01)

(58) Field of Classification Search
None
See application file for complete search history.

(56) References Cited

U.S. PATENT DOCUMENTS

| 3,583,993 A | 6/1971 | Okamoto et al. |
| 2013/0261147 A1 * | 10/2013 | Yang et al. ................... 514/287 |

FOREIGN PATENT DOCUMENTS

| JP | 11-255650 | | 9/1999 |
| JP | 11255650 A | * | 9/1999 |
| WO | 2006-099635 | | 9/2006 |
| WO | 2006-122723 | | 11/2006 |

OTHER PUBLICATIONS

"Acetylcholinesterase inhibitory activity of some Amaryllidaceae alkaloids and Narcissus extracts" by Lopez et al., Life Sci. 71, 2521-59 (2002).*
"Acetylcholinesterase Enzyme Inhibitory Effects of Amaryllidacae Alkalkoids" by Elgorashi et al., Planta Med. 70, 260-62 (2004).*
Heredity, vol. 48, No. 9, pp. 48-52, Sep. 1994.
Nehir Unver, "New skeletons and new concepts in Amaryllidaceae alkaloids" vol. 6, No. 1, Feb. 27, 2007, pp. 125-135.

* cited by examiner

*Primary Examiner* — Theodore R West
(74) *Attorney, Agent, or Firm* — Lexyoume IP Meister PLLC

(57) ABSTRACT

Provided are novel use of an extract of *Lycoris chejuensis* or a compound isolated therefrom for inhibition of β-amyloid production and/or prevention, improvement and/or treatment of a neurodegenerative disease, more specifically a β-amyloid production inhibitor, and/or a composition for prevention or treatment of a neurodegenerative disease containing one or more kinds selected from the group consisting of an extract of *Lycoris chejuensis*, and/or dihydrolycoricidine, 2-methoxypancracine, lycoricidine, and/or lycoricidinol, as an active ingredient; a method for inhibiting β-amyloid production, and/or preventing and/or treating a neurodegenerative disease using the same; and, a method for preparing the same.

7 Claims, 12 Drawing Sheets

METHOD OF PREVENTING AND/OR TREATING A NEURODEGENERATIVE DISEASE BY ADMINISTERING AN EXTRACT OF *LYCORIS CHEJUENSIS* AND/OR A COMPOUND ISOLATED THEREFROM

CROSS-REFERENCE TO RELATED APPLICATION

This application claims priority to and the benefit of Korean Patent Application No. 10-2009-0018520 filed in the Korean Intellectual Property Office on Mar. 4, 2009, the entire contents of which are incorporated herein by reference.

BACKGROUND OF THE INVENTION (a) Field of the Invention

A novel use of an extract of *Lycoris chejuensis* or a compound isolated therefrom for inhibition of β-amyloid production and/or prevention, improvement and/or treatment of a neurodegenerative disease is provided. More specifically, an inhibitor against β-amyloid production, and/or a composition for prevention and/or treatment of a neurodegenerative disease, containing one or more selected from the group consisting of an extract of *Lycoris chejuensis*, dihydrolycoricidine, 2-methoxypancracine, lycoricidine, and lycoricidinol, as an active ingredient; a method of inhibiting β-amyloid production, and/or preventing and/or treating a neurodegenerative disease, using the same; and, a method for preparing the same, are provided.

(b) Description of the Related Art

Dementia which is one of representative neurodegenerative diseases refers to symptoms characterized by deterioration of normal brain functions including intelligence such as memory, cognition, comprehension, computation abilities, learning skills, language abilities, judgment, and the like, due to brain cell damage caused by various reasons. Senile dementia which is age-related mental disorder resulted from degenerative change of brain mainly occurs in old age from about 65 to 70 years old.

Alzheimer's disease becomes most important senile dementia, and has been known to be mainly caused by accumulation of β-amyloid in brain and neurotoxicity resulted therefrom. In particular, β-amyloid forms plaque in which proteins are accumulated and aggregated in brain, causes Alzheimer's disease. The Alzheimer's disease exhibits pathohistological characteristics such as overall brain atrophy, cerebral ventricular expansion, neurofibrillary tangle, senile plaque, and the like, decreased intellectual functions including memory, judgment and language skills, and the like, and behavior disorders, and it may be involved with psychiatric symptoms such as depression. In addition, the above symptoms may be gradually advanced to lead death 6 to 8 years after attack of disease.

β-amyloid is known to be produced from amyloid precursor protein(APP) by continuous actions of membrane protein hydrolytic enzymes, β-secretase(BACE1) and γ-secretase. β-amyloid is largely classified into 2 types, $A\beta_{40}$ and $A\beta_{42}$, each of which consists of 40 or 42 amino acids. Although most of β-amyloid is $A\beta_{40}$, relatively less formed $A\beta_{42}$ easily makes plaque, and thus, it has been designated as a most important causative agent.

Tacrine (Cognex, 1994) and donepezil (Aricept, 1996), which are FDA approved drugs, have been used as representative anti-dementia drugs. The mechanisms of these drugs are known to increase neurotransmitter acetylcholine by inhibiting the activity of acetylcholine esterase (AChE), which is hydrolytic enzyme of acetylcholine that plays an important part in the central nervous pathway, thereby preventing and treating dementia. However, tacrine is expensive compared to the efficacy and may cause serious hepatotoxicity, and donepezil may stimulate parasympathetic nerves to cause various side effects such as vomiting, nausea, diarrhea, etc. In addition, these drugs are not for fundamental treatment such as improvement of brain disease, but only for alleviation of main symptoms of dementia such as memory impairment.

Therefore, studies on the development of novel anti-dementia drugs capable of fundamental treatment without side effects have been actively under progress. One approach is to develop material capable of blocking production of β-amyloid which is known to be a causative agent for Alzheimer's disease, but effective therapeutic agent has not been developed yet.

Meanwhile, dihydrolycoricidine, which is mainly contained in *Hymenocallis littoralis*, *Hymenocallis latifolia*, and the like, has been known to exhibit anti-virus and anti-cancer effects, but it has not been reported to exhibit dementia prevention and treatment effects.

2-methoxypancracine, which is contained in *Hymenocallis* sp., has been known to exhibit anti-inflammatory, antioxidant, and antibacterial effects, but it has not been reported to exhibit dementia prevention and treatment effects.

In addition, lycoricidine and lycoricidinol, which are contained in *Narcissus* sp., *Lycoris* sp., *Pancratium* sp., *Haemanthus* sp., and the like, have been known to exhibit anti-viral and anticancer effects (Gabrielsen, B. et al. *J. Nat. Prod.* 55: 1569, 1992, Mondon, A. et al. *Chem. Ber.* 108: 445, 1975), but they have not been reported to exhibit β-amyloid production inhibiting effects or dementia prevention and treatment effects.

Meanwhile, *Lycoris chejuensis*, which is a white plant belonging to *Amaryllidaceae* and distributed only in Cheju, South Korea, has been recently named (Tae and Ko, Kor. J. Pl. Tax. 23: 233, 1993). However, there have been insufficient studies on chemical analysis or physiological activity and clinical effects thereof.

SUMMARY OF THE INVENTION

The inventors, during studying on the development of a therapeutic agent having excellent therapeutic effect for a neurodegenerative disease without side effects and capable of fundamental treatment, found that an extract of *Lycoris chejuensis*, or a compound isolated therefrom, such as dihydrolycoricidine, 2-methoxypancracine, lycoricidine or lycoricidinol, inhibits the production of β-amyloid and β-secretase product(sAPPβ), thereby being effective for prevention or treatment of dementia, a representative neurodegenerative disease, to completed the present invention.

Accordingly, certain embodiments provide a composition for preventing and/or treating a neurodegenerative disease containing an extract of *Lycoris chejuensis* as an active ingredient; a use of the extract of *Lycoris chejuensis*, for the prevention and/or treatment of a neurodegenerative disease; a use of the extract of *Lycoris chejuensis*, for the manufacture of a composition for prevention and/or treatment of a neurodegenerative disease; and a method of preventing and/or treating a neurodegenerative disease comprising administering the extract of *Lycoris chejuensis* to a patient in need of prevention and/or treatment of a neurodegenerative disease.

Certain embodiments provide a composition for preventing and/or treating a neurodegenerative disease containing one or more selected from the group consisting of dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof, as an active ingredient; a use of one or more selected from the group consisting of dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof, for the prevention and/or treatment of a neurodegenerative disease; a use of one or more selected from the group consisting of dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof, for the manufacture of a composition for prevention and/or treatment of a neurodegenerative disease; and a method of preventing and/or treating a neurodegenerative disease comprising administering one or more selected from the group consisting of dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof, to a patient in need of prevention and/or treatment of a neurodegenerative disease.

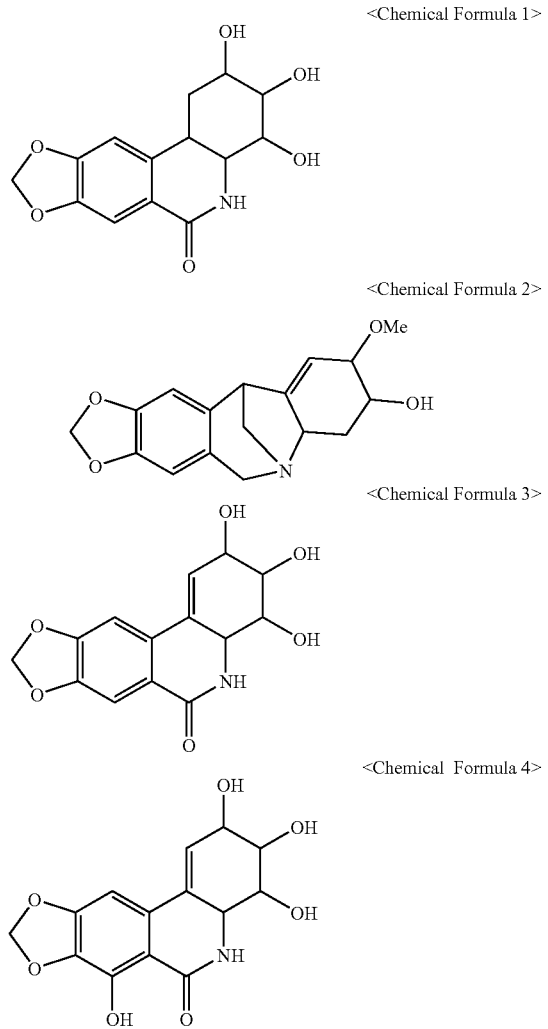

<Chemical Formula 1>

<Chemical Formula 2>

<Chemical Formula 3>

<Chemical Formula 4>

Certain embodiments provide a β-amyloid production inhibitor containing one or more selected from the group consisting of an extract of *Lycoris chejuensis*, dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof; a use of one or more selected from the group consisting of an extract of *Lycoris chejuensis*, dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof, for inhibiting β-amyloid production; a use of one or more selected from the group consisting of an extract of *Lycoris chejuensis*, dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof, for the manufacture of a β-amyloid production inhibitor; and a method of inhibiting β-amyloid production comprising administering one or more selected from the group consisting of an extract of *Lycoris chejuensis*, dihydrolycoricidine of Chemical Formula 1, 2-methoxypancracine of Chemical Formula 2, lycoricidine of Chemical Formula 3, lycoricidinol of Chemical Formula 4, and pharmaceutically acceptable salts thereof, to a patient in need of inhibition of β-amyloid production.

Certain embodiments provide a method of preparing an extract of *Lycoris chejuensis* having the effect of inhibiting β-amyloid production, comprising the steps of:

(i) extracting *Lycoris chejuensis* with one or more solvents selected from the group consisting of water and $C_1$ to $C_4$ lower alcohol; and optionally, (ii) additionally extracting the extract obtained in the step (i) with or more solvents selected from the group consisting of water, hexane, methylene chloride, ethyl acetate, and $C_1$ to $C_4$ lower alcohol; and optionally, (iii) additionally extracting the extract obtained in the step (ii) with one or more solvents selected from the group consisting of acetonitrile, $C_1$ to $C_4$ lower alcohol, acetone, and water.

Certain embodiments provide a method of preparing dihydrolycoricidine of Chemical Formula 1 and/or lycoricidine of Chemical Formula 3 from *Lycoris chejuensis*, comprising the steps of:

(a) extracting *Lycoris chejuensis* with one or more solvents selected from the group consisting of water and $C_1$ to $C_4$ lower alcohol, (b) additionally extracting the extract obtained in step (a) with one or more solvents selected from the group consisting of water, hexane, methylene chloride, ethyl acetate and $C_1$ to $C_4$ lower alcohol, and (c) performing reverse phase column chromatography for the extract obtained in step (b) using a mixed solvent of water and one or more organic solvents selected from the group consisting of acetonitrile, methanol, and acetone, in a volume ratio of 1~7:10, preferably 3~7:10, more preferably 5~7:10 (the volume of the organic solvent(s): the volume of water).

Certain embodiments provide a method for preparing 2-methoxypancracine of Chemical Formula 2 and/or lycoricidinol of Chemical Formula 4 from *Lycoris chejuensis*, comprising the steps of:

(a') extracting *Lycoris chejuensis* with one or more solvents selected from the group consisting of water and $C_1$ to $C_4$ lower alcohol.

(b') additionally extracting the extract obtained in step (a') with one or more solvents selected from the group consisting of water, hexane, methylene chloride, ethyl acetate, and $C_1$ to $C_4$ lower alcohol, and (c') performing reverse phase column chromatography for the extract obtained in step (b') using a mixed solvent of water and one or more organic solvents selected from the group consisting of acetonitrile, methanol, and acetone, in a volume ratio of 7.1~15:10, preferably 9~15:10, more preferably 11~15:10, still more preferably 13~15:10 (the volume of the organic solvent(s): the volume of water).

DETAILED DESCRIPTION OF THE EMBODIMENTS

Figure 1:
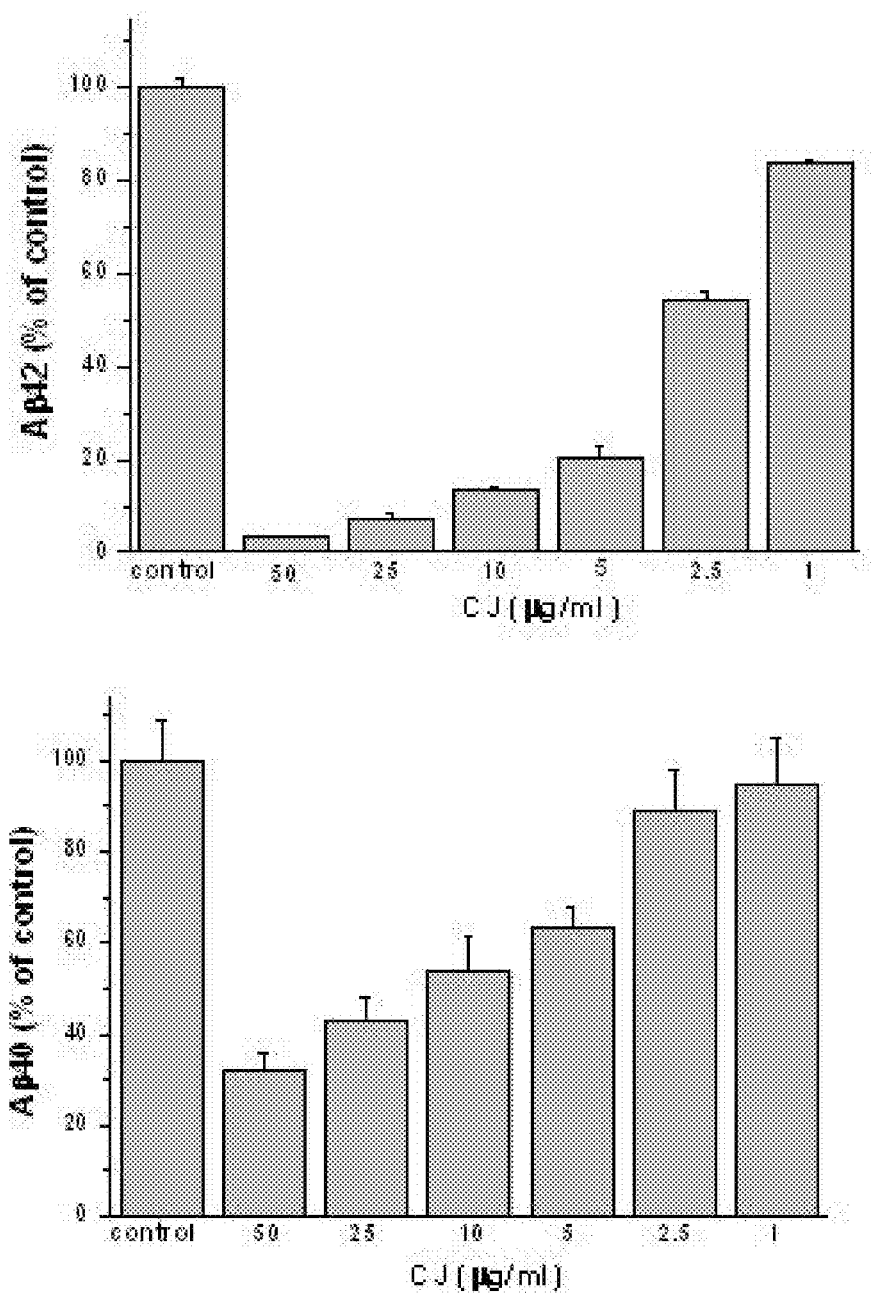
FIG. 1 is a graph showing the effect of an ethanol extract of *Lycoris chejuensis* (CJ) for inhibiting β-amyloid($A\beta_{40}$, $A\beta_{42}$) production according to concentration.

An extract of *Lycoris chejuensis*, although not limited hereto, may be prepared by any extraction method known in the art using a bulb or root of *Lycoris chejuensis*. For example, the extraction method may include heat extraction, ultrasonic extraction, filtration, pressure extraction, reflux extraction, supercritical extraction, electric extraction, and the like. If necessary, after the extraction, concentration and/or lyophilization may be additionally conducted.

The extract of *Lycoris chejuensis* may be obtained by extracting *Lycoris chejuensis* with one or more extraction solvents selected from the group consisting of water and $C_1$ to $C_4$ lower alcohol, and for example, 70 to 100% (v/v) of $C_1$ to $C_4$ lower alcohol may used as the extraction solvent. The extraction solvent may be used in the amount of 1 to 5 times by volume of the *Lycoris chejuensis*, but not limited thereto, and, the extraction time may be 1 to 12 hours, preferably 2~5 times, but not limited thereto.

Preferably, the extract of *Lycoris chejuensis* may be prepared by (i) extracting *Lycoris chejuensis* with one or more extraction solvents selected from the group consisting of water and $C_1$ to $C_4$ lower alcohol, and then, (ii) additionally extracting the extract obtained in step (i) with one or more extraction solvents selected from the group consisting of water, hexane, methylene chloride, ethyl acetate, and $C_1$ to $C_4$ lower alcohol. For example, the $C_1$ to $C_4$ lower alcohol may be butanol, but not limited thereto.

Most preferably, the extract of *Lycoris chejuensis* may be prepared by (iii) additionally extracting the extract obtained in step (ii) with one or more kinds selected from the group consisting of acetonitrile, $C_1$ to $C_4$ lower alcohol, acetone, and water. More preferably, the extract of *Lycoris chejuensis* may be prepared by extracting the extract obtained in step (ii) with a mixed solvent of acetone and water, where the volume ratio of acetone and water in the mixed solvent may be 1:4 to 4:1 (the volume of acetone: the volume of water), but not limited thereto.

According to one embodiment of the invention, an ethanol extract of *Lycoris chejuensis* may be prepared by adding ethanol to the root of *Lycoris chejuensis* and concentrating under reduced pressure(see <Example 1-1>). In addition, the obtained ethanol extract of *Lycoris chejuensis* may additionally extracted with each of water, hexane, methylene chloride, and butanol, to obtain a hexane fraction, a methylene chloride fraction, a butanol fraction, and a water fraction, respectively (see <Example 1-2>). The butanol fraction, which is shown to have most excellent amyloid inhibition effect among the above fractions, may additionally extracted with acetone, water or a mixed solvent of acetone and water, to obtain butanol sub-fractions (see <Example 1-2>).

The active ingredient, dihydrolycoricidine, 2-methoxypancracine, lycoricidine, or lycoricidinol, may be used in itself or in the form of pharmaceutically acceptable salts thereof. For the salts, pharmaceutically acceptable acid addition salts formed by free acid may be preferable. For the free acid, an organic acid or an inorganic acid may be used. The organic acid may include any pharmaceutically acceptable organic acid, such as citric acid, acetic acid, lactic acid, tartaric acid, maleic acid, fumaric acid, formic acid, propionic acid, oxalic acid, trifluoroacetic acid, benzoic acid, gluconic acid, methasulfonic acid, glycolic acid, succinic acid, 4-toluensulfonic acid, glutamic acid, aspartic acid, and the like, but not limited thereto. The inorganic acid may include any pharmaceutically acceptable inorganic acid, such as hydrochloric acid, bromic acid, sulfuric acid, phohporic acid, and the like, but not limited thereto.

Dihydrolycoricidine, 2-methoxypancracine, lycoricidine, or lycoricidinol may be isolated from a natural substance containing the compound by any extraction and isolation method known in the art, or chemically synthesized by any synthesis method known in the art. In addition, it may be prepared by extracting and isolating from the whole plant of *Lycoris chejuensis*.

According to one experimental example, it was revealed that when HeLa cell line, that is transfected with amyloid precursor protein(APP), was treated with the ethanol extract of *Lycoris chejuensis*, β-amyloid production in the cell line was effectively inhibited (see <Experiment 1-1>). The same results were obtained in the hexane fraction, the methylene chloride fraction, the butanol fraction, and the water fraction of *Lycoris chejuensis* (see <Experimental Example 1-2>). The same result was also obtained in the butanol sub-fractions of *Lycoris chejuensis* (see <Experimental Example 1-2>).

According to another experimental example, it was revealed that, when HeLa cell line, that is transfected with amyloid precursor protein(APP), was treated with dihydrolycoricidine, 2-methoxypancracine, lycoricidine, or lycoricidinol, β-amyloid production in the cell line was effectively inhibited (see <Experiment 3>).

According to another experimental example, in order to examine the reason of the inhibition of β-amyloid production, the production of β-secretase product (sAPPβ) was quantified. As the result, it was found that the production of β-secretase product (sAPPβ) was inhibited by dihydrolycoricidine. Thus, it can be seen that dihydrolycoricidine inhibits β-secretase activity, to decrease the production of β-secretase product (sAPPβ), thereby inhibiting β-amyloid production(see <Experiment 4>).

The extract of *Lycoris chejuensis* and dihydrolycoricidine, 2-methoxypancracine, lycoricidine, and/or lycoricidinol, which is isolated therefrom, have activities to effectively inhibit β-amyloid($A\beta_{40}$, $A\beta_{42}$) production, and thus, they may be useful for β-amyloid inhibition, and/or prevention, improvement or treatment of related diseases.

The neurodegenerative disease may include any diseases occurred due to degeneration of nerves, particularly cranial nerves, for examples, one or more selected from the group consisting of dementia, Parkinson's disease, Alzheimer's disease, Huntington's disease, Pick's Disease, Parkinson's disease-ALS(amyotrophic lateral sclerosis)-dementia complex, and the like. According to one embodiment, the neurodegenerative disease may be dementia, particularly Alzheimer's disease.

The content of the extract of *Lycoris chejuensis*, dihydrolycoricidine, 2-methoxypancracine, lycoricidine, and/or lycoricidinol as an active ingredient of the composition of the present invention may be appropriately controlled depending upon the formulated form, purpose, patient condition, and kind and severity of symptoms, and the like, and for example, it may be 0.001 to 99.9 wt %, preferably 0.1 to 50 wt %, based on the weight of the composition, but not limited thereto. The content of the extract of *Lycoris chejuensis* is based on solid weight, wherein the solid weight means weight of the ingredients that remains after removing a solvent in the extract.

The composition of the present invention can be administered to mammals including human in various routes. It can be administered using commonly used method, for examples, it can be administered orally, intrarectally, or through intravenous, intramuscular, subcutaneous, intrauterine, or intracerebroventricular injection. The composition can be formulated into an oral form, such as powder, granule, tablet, capsule, suspension, emulsion, syrup, aerosol, etc., or a parenteral form, such as transdermal agent, suppository, sterile injection solution, etc.

The composition of the present invention may further comprise a pharmaceutically and physiologically acceptable adjuvant such as carriers, excipients and diluents, in addition to the active ingredient, the extract of *Lycoris chejuensis*, dihydrolycoricidine, 2-methoxypancracine, lycoricidine, and/or lycoricidinol. The carriers, excipients and diluents may be one or more selected from the group consisting of lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, and the like.

For the formulation of the composition, conventionally used diluents, excipients, and the like, such as a filler, thickner, a binder, a wetting agent, a disintegrator, a surfactant, and the like may be used. A solid preparation for oral administration may be a tablet, a pill, powders, granules, a capsule, and the like, and it may be prepared by mixing one or more excipients, for examples, starch, calcium carbonate, sucrose or lactose, gelatin, and the like with the active ingredient. A lubricant such as magnesium stearate and/or talc may be used in addition to the excipients. A liquid preparation for oral administration may be a suspension, liquids for internal use, an emulsion, a syrup, and the like, and it may include conventionally used diluents such as water or liquid paraffin, and/or various excipients, such as a wetting agent, a sweetener, an aromatic, a preservative, and the like. A preparation for parenteral administration may be a sterilized aqueous solution, a nonaqueous solvent, a suspension, an emulsion, a lyophilizate, a suppository, a transdermal preparation, and the like. The nonaqueous solvent or suspension may include vegetable oil such as propylene glycol, polyethylene glycol, olive oil, and/or injectable ester such as ethyl oleate. As a base of the suppository, witepsol, macrogol, tween 61, cacao butter, laurine better, glycerogelatin, and the like can be used.

The dosage of the composition of the present invention may be varied depending upon the age, weight, sex, administration method, health condition and disease severity of the patient, and it may be administered once or several times a day at a regular interval according to judgment of a physician or pharmacist. For example, the daily dose may be 0.5 to 50 mg/kg, preferably 1 to 30 mg/kg, based on the content of the active ingredient. The dosage is illustrative of the average, and it may be higher or lower depending upon the individual variation. If the daily dose of the composition of the present invention is less than the above range, it will be difficult to achieve a desired effect, and if it exceeds the above range, it exceeds commonly used range to cause undesirable side effect as well as being uneconomical.

The patient may be mammals including human, for examples, human in need of treatment of a neurodegenerative disease, for example, dementia, Parkinson's disease, Alzheimer's disease, Huntington's disease, Pick's Disease, Parkinson's disease-ALS(amyotrophic lateral sclerosis)-dementia complex, and the like, and particularly Alzheimer's disease.

A health functional food of the present invention may be all types of foods, such as various functional foods, nutritional supplements, food additives, and the like, having the effect of prevention and/or improvement of a neurodegenerative disease. The food composition may be prepared in various types according to any conventional methods known in the art.

A method of preparing dihydrolycoricidine of Chemical Formula 1 and/or lycoricidine of Chemical Formula 3 comprises the steps of: (a) extracting *Lycoris chejuensis* with one or more selected from the group consisting of water and an organic solvent, (b) additionally extracting the extract prepared in step (a) with one or more selected from the group consisting of water, hexane, methylene chloride, ethyl acetate, and $C_1$ to $C_4$ lower alcohol, and (c) performing reverse phase column chromatography for the extract prepared in step (b) using a mixed solvent of water and one or more organic solvents selected from the group consisting of acetonitrile, methanol, and acetone, in a volume ratio of 1~7:10 (the volume of the organic solvent(s): the volume of water).

A method of preparing 2-methoxypancracine of Chemical Formula 2 and/or lycoricidinol of Chemical Formula 4 comprises the steps of: (a') extracting *Lycoris chejuensis* with one or more selected from the group consisting of water and an organic solvent; (b') additionally extracting the extract prepared in step (a') with one or more selected from the group consisting of water, hexane, methylene chloride, ethyl acetate, and $C_1$ to $C_4$ lower alcohol; and, (c') performing reverse phase column chromatography for the extract prepared in step (b') using a mixed solvent of water, and one or more kinds of an organic solvent selected from the group consisting of acetonitrile, methanol and acetone, in a volume ratio of 7.1~15:10 (the volume of the organic solvent(s):the volume of water).

Specifically, in step (a) or (a'), an extract of *Lycoris chejuensis* may be prepared using the whole plant of *Lycoris chejuensis* by any conventional extraction method known in the art. The extraction method may include heat extraction, ultrasonic extraction, filtration, pressure extraction, reflux extraction, supercritical extraction, electrical extraction, and the like. If necessary, after the extraction, concentration or lyophilization may be additionally conducted. The organic solvent used in step (a) or (a') may be preferably $C_1$ to $C_4$ lower alcohol, but not limited thereto. The water or organic solvent may be preferably used in 1 to 5 times by volume of the *Lycoris chejuensis*, and extraction time may be 1 to 12 hours, preferably 2~5 hours, but not limited thereto.

In the step (b) or (b'), the extract prepared in step (a) or (a') is additionally extracted with one or more selected from the group consisting of water, hexane, methylene chloride, ethyl acetate, and $C_1$ to $C_4$ lower alcohol, to obtain each solvent fraction. The $C_1$ to $C_4$ lower alcohol is preferably butanol, but not limited thereto.

The reverse phase column chromatography in step (c) or (c') may be performed, for example, by sequentially conducting HP-20 reverse phase column chromatography and C18 reverse column chromatography, but not limited thereto. For example, the extract prepared in step (b) or (b') may be subjected to HP-20 reverse phase column chromatography using one or more selected from the group consisting of acetonitrile, methanol, acetone, and water as an eluent with changing the concentration of acetonitrile, methanol, or acetone.

More specifically, for the preparation of dihydrolycoricidine and/or lycoricidine, HP-20 reverse phase column chromatography may be conducted using acetone and water in a volume ratio of 3~7:10, and for the preparation of 2-methoxypancracine and/or lycoricidinol, HP-20 reverse phase column chromatography may be conducted using acetone and water in a volume ratio of a 7.1~15:10. Preferably, for the preparation of dihydrolycoricidine and/or lycoricidine, HP-20 reverse phase column chromatography may be conducted using acetone and water in a volume ratio of 1:1.5, and for the preparation of 2-methoxypancracine and/or lycoricidinol, HP-20 reverse phase column chromatography may be conducted using acetone and water in a volume ratio of a 1:0.67.

Subsequently, C18 reverse column chromatography may be conducted to prepare dihydrolycoricidine, 2-methoxypancracine, lycoricidine, and/or lycoricidinol. More preferably, C18 reverse column chromatography may be conducted using a mixed solution of acetonitrile (containing 0.02 vol % of trifluoroacetic acid) and water as an eluent with changing the concentration of acetonitrile to prepare dihydrolycoricidine, 2-methoxypancracine, lycoricidine, and/or lycoricidinol.

As described above, since dihydrolycoricidine, 2-methoxypancracine, lycoricidine, lycoricidinol, or an extract of *Lycoris chejuensis* has excellent effect of inhibiting the production of β-amyloid and β-secreatase product(sAPPβ), it may be useful for prevention and/or treatment of nerve cell toxicity induced by β-amyloid and β-secretase product (sAPPβ), and neurodegenerative diseases caused thereby.

EXAMPLES

The present invention is further explained in more detail with reference to the following examples. These examples, however, should not be interpreted as limiting the scope of the present invention in any manner.

Example 1

Preparation of an Extract of *Lycoris Chejuensis* cl
1-1 Preparation of an Ethanol Extract of *Lycoris Chejuensis*

A bulb of *Lycoris chejuensis* collected in Jeju Island was dried, to prepare *Lycoris chejuensis* sample. 590 g of the obtained sample was cut into small pieces and introduced in a vessel for extraction. Then, 95% (v/v) ethanol was added thereto in 2 times by volume of the sample. The reaction mixture was reflux extracted for 3 hours, cooled at room temperature and filtrated. The filtrated extract was concentrated at 40° C. under reduced pressure until the solvent was completely evaporated, to obtain 200 g of an ethanol extract of *Lycoris chejuensis* (hereinafter referred to as 'CJ') (yield: 34%)<cl 1-2 Preparation of Fractions of *Lycoris Chejuensis*

200 g of the ethanol extract of *Lycoris chejuensis* prepared in Example <1-1> was suspended in 1 L of water, and then, 1 L of each of hexane, methylene chloride and butanol was sequentially added each twice to conduct solvent fraction, thereby obtaining 1 g of hexane fraction (hereinafter referred to as 'CJ-1'), 1 g of methylene chloride fraction (hereinafter referred to as 'CJ-2'), 5.5 g of butanol fraction (hereinafter referred to as 'CJ-3'), and 182 g of water fraction (hereinafter referred to as 'CJ-4').

From the obtained 5.5 g of butanol fraction of *Lycoris chejuensis*, butanol sub-fractions of *Lycoris chejuensis* were prepared using acetone, water or a mixed solvent of acetone and water. In particular, reverse chromatography was conducted using HP-20 200 g as a stationary phase and acetone, water, or a mixture of acetone and water with various volume ratios (acetone:water) of 0:10 (water only), 2:8, 4:6, 6:4, 8:2 and 10:0(acetone only), to obtain 8 kinds of butanol sub-fractions of *Lycoris chejuensis* [hereinafter referred to as CJ-3-F1 (water only, 400 ml), CJ-3-F2 (acetone:water=2:8, 400 ml), CJ-3-F3 (acetone:water=4:6, the first part 200 ml), CJ-3-F4 (acetone:water=4:6, the later part 200 ml), CJ-3-F5 (acetone:water=6:4, the first part 200 ml), CJ-3-F6 (acetone:water=6:4, the later part 200 ml), CJ-3-F7 (acetone:water=8:2, 400 ml), and CJ-3-F8 (acetone only, 400 ml), respectively].

Example 2

Isolation and Identification of Compounds from the Extract of *Lycoris Chejuensis*

2-1 Isolation and Identification of Dihydrolycoricidine and Lycoricidine

Figure 14:
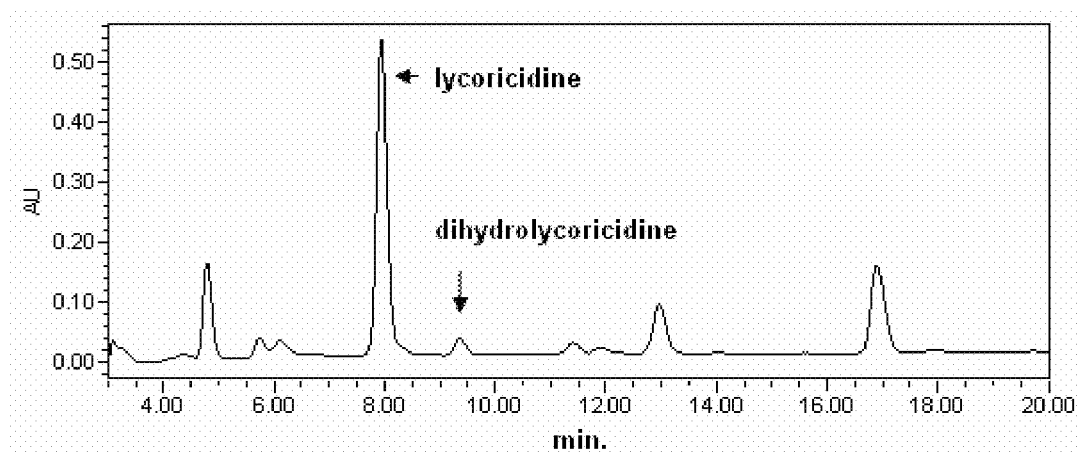
FIG. 14 shows the result of HPLC chromatogram of a butanol sub-fraction of *Lycoris chejuensis* obtained using a mixture solvent of acetone and water in the volume ratio of 4:6 (the volume of acetone: the volume of water).

Among the 8 butanol sub-fractions prepared in Example <1-2>, the sub-fraction obtained using the mixture of acetone and water in the volume ratio of 4:6 (the volume of acetone: the volume of water, CJ-3-F3+CJ-3-F4) was subjected to HPLC chromatogram (UV wavelength of 210 nm, mobile phase 10 vol. % acetonitrile/water~20 vol. % acetonitrile/water, 20 min., for analysis), and the obtained result was shown in FIG. 14. As shown in FIG. 14, it was found that dihydrolycoricidine and lycoricidine are contained in the sub-fraction.

The butanol sub-fraction obtained using the mixture of acetone and water in the volume ratio of 4:6 (the volume of acetone: the volume of water) in the Example <1-2> was concentrated under reduced pressure, and then, subjected to high performance liquid chromatography using C18 reverse phase column, and using a mixed solution of acetonitrile (containing 0.02 vol % of trifluoroacetic acid) and water as an eluent, to purify the compounds. In particular, high performance liquid chromatography using C18 reverse phase column (preparative) was performed using concentration gradient where the concentration of acetonitrile increases from 10 vol. % acetonitrile/water to 20 vol. % acetonitrile/water for 40 minutes. As the result, two kinds of compounds were purified from 200 g of the alcohol extract of Lycoris chejuensis, in the amount of 10 mg (yield: 0.005%) and 40 mg (yield: 0.02%), respectively.

In order to identify the obtained compound with the yield of 0.005%, NMR analysis and mass spectrometry were performed. In particular, molecular weight was determined to be 273 by MS measurement using Agilent 1100 high performance liquid chromatography-mass spectrometer (HPLC-ESI-MS), and molecular formula was identified as dihydrolycoricidine of following Chemical Formula 1 by $^1$H and $^{13}$C-NMR spectrum analysis using nuclear magnetic resonance (Varian 500 MHz NMR) (George R. T. and Noeleen M. J. Nat. Prod 68: 207-211, 2005), of which concrete analysis results were as follows.

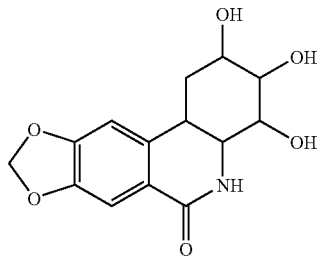

<Chemical Formula 1>

Light yellow semi-solid material; Molecular Formula $C_{14}H_{15}NO_6$; ESI-MS: m/z 274 [M+H]$^+$;
$^1$H NMR (500 MHz, CD$_3$OD): δ 1.86(1H, td, J=13.0, 3.0 Hz, H-1$_{ax}$), 2.27(1H, dt, J=13.0, 3.0 Hz, H-1$_{eq}$), 3.07(1H, td, J=13.0, 3.0 Hz, H-10b), 3.49(1H, dd, J=13.0, 10.0 Hz, H-2), 3.89(1H, dd, J=10.0, 3.0 Hz, H-3), 3.92(1H, dd, J=3.0, 3.0 Hz, H-4), 4.10(1H, dt, J=3.0, 3.0 Hz, H-4a), 6.03 and 6.05(each 1H, d, J=1.5 Hz, OCH$_2$O), 6.90(1H, br s, H-10), 7.40(1H, s, H-7). Exchangeable Proton Signal (500 MHz, DMSO-d$_6$) δ 7.30(1H, br s, NH), 5.00 (1H, br s, OH), 4.58(1H, br s, OH), 4.56(1H, br s, OH); $^{13}$C NMR (125 MHz, DMSO-d$_6$): δ 30.3 (C-1), 32.7 (C-10b), 58.2 (C-4-a), 69.3 (C-2), 70.2 (C-3), 74.0 (C-4), 102.5 (OCH$_2$O), 104.9 (C-10), 107.2 (C-7), 124.5 (C-6a), 138.8 (C-10a), 146.5 (C-8), 151.0 (C-9), 165.0 (C-6).

In order to identify the obtained compound with the yield of 0.02%, NMR analysis and mass spectrometry were performed.

In particular, molecular weight was determined to be 291 by MS measurement using Agilent 1100 high performance liquid chromatography-mass spectrometer (HPLC-ESI-MS), and molecular formula was identified as lycoricidine of following Chemical Formula 3 by $^1$H-NMR spectrum analysis using nuclear magnetic resonance (Varian 500 MHz NMR) (George R. T. and Noeleen M. J. Nat. Prod 68: 207-211, 2005, which is incorporated herein as a reference), of which concrete analysis results were as follows.

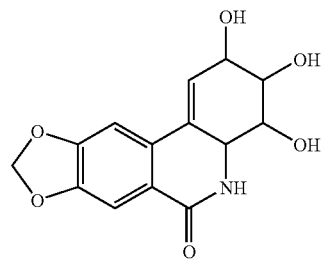

<Chemical Formula 3>

Light yellow semi-solid material; Molecular Formula $C_{14}H_{13}NO_6$; ESI-MS: m/z 292 [M+H]$^+$ $^1$H NMR (500 MHz, CD$_3$OD): δ 3.92 (1H, m, H-3), 3.94 (1H, m, H-4), 4.26 (1H, ddd, J=4.5, 2.0, 1.5 Hz, H-2), 4.40 (1H, ddt, J=9.5, 2.5, 1.0 Hz, H-4a), 6.06 and 6.08 (each 1H, d, J=1.0 Hz, —OCH$_2$O—), 6.18 (1H, m, H-1), 7.17 (1H, s, H-10), 7.40 (1H, s, H-7).

2-2 Isolation and Identification of 2-methoxypancracine and Lycoricidinol

Figure 15:
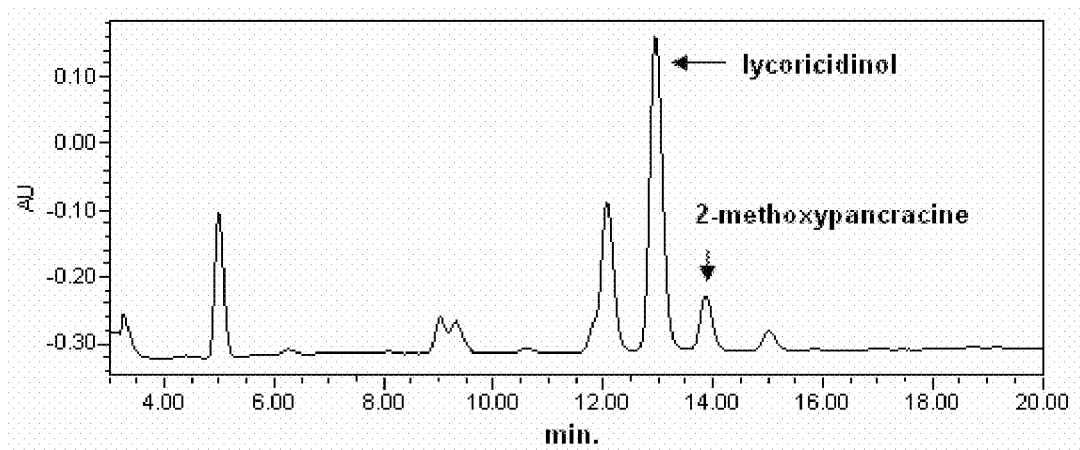
FIG. 15 shows the result of HPLC chromatogram of a butanol sub-fraction of *Lycoris chejuensis* obtained using a mixture solvent of acetone and water in the volume ratio of 6:4 (the volume of acetone: the volume of water).

Among the 8 butanol sub-fractions prepared in Example <1-2>, the sub-fraction obtained using the mixture of acetone and water in the volume ratio of 6:4 (the volume of acetone: the volume of water; CJ-3-F5+CJ-3-F6) was subjected to HPLC chromatogram (UV wavelength of 210 nm, mobile phase 10 vol. % acetonitrile/water~20 vol. % acetonitrile/water, 20 min., for analysis), and the obtained result was shown in FIG. 15. As shown in FIG. 15, it was found that 2-methoxypancracine and lycoricidinol are contained in the sub-fraction.

The butanol sub-fraction obtained using the mixture of acetone and water in the volume ratio of 6:4 (the volume of acetone: the volume of water) in the Example <1-2> was concentrated under reduced pressure, and then, subjected to high performance liquid chromatography using C18 reverse phase column, and using a mixed solution of acetonitrile (containing 0.02 vol % of trifluoroacetic acid) and water as an eluent, to purify the compounds. In particular, high performance liquid chromatography using C18 reverse phase column (preparative) was performed using concentration gradient where the concentration of acetonitrile increases from 10 vol. % acetonitrile/water to 20 vol. % acetonitrile/water for 40 minutes. As the result, two kinds of compounds were purified from 200 g of the alcohol extract of Lycoris chejuensis, in the amount of 3 mg (yield: 0.0015%) and 80 mg (yield: 0.04%), respectively.

In order to identify the obtained compound with the yield of 0.0015%, NMR analysis and mass spectrometry were performed. In particular, molecular weight was determined to be 301 by MS measurement using Agilent 1100 high performance liquid chromatography-mass spectrometerHPLC-ESI-MS), and molecular formula was identified as 2-methoxypancracine of following Chemical Formula 2 by $^1$H-NMR spectrum analysis using nuclear magnetic resonance(Varian 500 MHz NMR) (Ishizaki M. et al. J. Org. Chem. 57: 7285-7295, 1992, which is incorporated herein as a referenc), of which concrete analysis results are as follows.

<Chemical Formula 2>

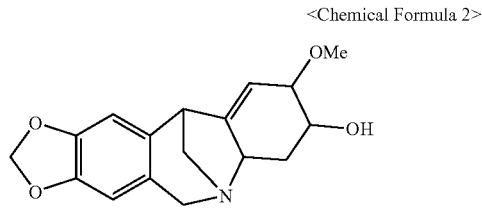 [SMILES: COC1C=C2C3CN(Cc4cc5c(cc43)OCO5)C2CC1O]

Light yellow semi-solid material; Molecular Formula $C_{17}H_{19}NO_4$; ESI-MS: m/z 302 [M+H]$^+$ $^1$H NMR (500 MHz, CD$_3$OD): δ 1.45 (1H, dt, J=12.5, 3.0 Hz, H$_2$-4), 2.12 (1H, m, H$_2$-4), 3.05 (2H, m, H-12), 3.38 (1H, d, J=2.5 Hz, H-11), 3.43 (3H, s, 3-OMe), 3.45 (1H, m, H-4a), 3.47 (1H, m, H-2), 3.82 (1H, d, J=16.5 Hz, H-6), 4.05 (1H, m, H-3), 4.31 (1H, d, J=16.5 Hz, H-6), 5.58 (1H, m, H-10), 5.87 and 5.88 (each 1H, d, J=1.0 Hz, OCH2O), 6.53 (1H, s, H-7), 6.61 (1H, s, H-10)

In order to identify the obtained compound with the yield of 0.04%, NMR analysis and mass spectrometry were performed.

In particular, molecular weight was determined to be 307 by MS measurement using Agilent 1100 high performance liquid chromatography-mass spectrometer (HPLC-ESI-MS), and molecular formula was identified as lycoricidinol of following Chemical Formula 4 by $^1$H-NMR spectrum analysis using nuclear magnetic resonance (Varian 500 MHz NMR) (George R. T. and Noeleen M. J. Nat. Prod 68: 207-211, 2005, which is incorporated herein as a referenc), of which concrete analysis results were as follows.

<Chemical Formula 4>

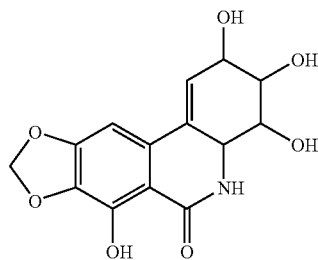

Light yellow semi-solid material; Molecular Formula $C_{14}H_{13}NO_7$; ESI-MS: m/z 308 [M+H]$^+$; $^1$H NMR (500 MHz, CD$_3$OD): δ 3.91 (1H, m, H-3), 3.92 (1H, m, H-4), 4.24 (1H, m, H-2), 4.36 (1H, m, H-4a), 6.03 and 6.05 (each 1H, d, J=1.0 Hz, —OCH$_2$O—), 6.18 (1H, m, H-1), 6.75 (1H, s, H-10).

Experimental Example 1

Effect of an Extract of Lycoris chejuensis to Inhibit β-amyloid Production 1-1 Effect of an Ethanol Extract of Lycoris Chejuensis to Inhibit β-amyloid Production In order to examine the effect of the ethanol extract of Lycoris chejuensis obtained in Example <1-1> to inhibit β-amyloid production, HeLa cell line transfected with human amyloid precursor protein(APP) was cultured in DMEM culture medium (Cat. #11995, Gibco, USA). The cell line was supplied by Prof. Tae-Wan Kim, Department of Pathology, Columbia University Medical Center, New York, N.Y.10032, USA.

To the cell culture solution, the ethanol extract of Lycoris chejuensis (CJ) obtained in Example <1-1> was added, and then, it was cultured at 37° C. for 8 hours, and the amount of β-amyloid secreted in the culture solution was measured. More specifically, in order to quantify β-amyloid, two kinds of β-amyloid (Aβ$_{40}$, Aβ$_{42}$), Human β-Amyloid [1-40] (Aβ$_{40}$) and Human β-Amyloid [1-42] (Aβ$_{42}$) Colorimetric ELISA kits (#KHB3482 and #KHB3442; BioSource International, Inc., USA) were respectively used. The results of quantifying β-amyloid are shown in following Table 1 and FIG. 1. The negative control means the case to which the extract of Lycoris chejuensis was not added.

TABLE 1

Effect of the ethanol extract of Lycoris chejuensis (CJ) to inhibit β-amyloid production

| | Concentration of CJ added (μg/ml) | | | | | |
|---|---|---|---|---|---|---|
| | 50 | 25 | 10 | 5 | 2.5 | 1 |
| Aβ42 production amount (%) compared to that of negative control (100%) | 3.5 ± 0.11 | 7.2 ± 0.10 | 13.6 ± 0.11 | 20.3 ± 2.39 | 54.4 ± 1.93 | 84.1 ± 0.54 |
| Aβ40 production amount (%) compared to that of negative control (100%) | 31.9 ± 3.65 | 43.2 ± 4.59 | 53.5 ± 8.24 | 63.5 ± 4.39 | 89.3 ± 8.99 | 94.4 ± 10.68 |

From the above Table 1 and FIG. 1, it can be seen that β-amyloid(Aβ$_{40}$, Aβ$_{42}$) production may be inhibited by the ethanol extract of Lycoris chejuensis(CJ) in a concentration dependent manner. cl 1-2 Effect of Fractions of Lycoris Chejuensis for Inhibiting β-amyloid Production The hexane fraction (CJ-1), methylene chloride fraction (CJ-2), butanol fraction (CJ-3), and water fraction (CJ-4) obtained in Example <1-2> were added each in an amount of 25 μg/ml, respectively, by the same procedure as described in Experimental example <1-1>, and β-amyloid (Aβ40, Aβ42) production was quantified. The obtained results are shown in following Table 2 and FIG. 2.

TABLE 2

Effect of fractions of *Lycoris chejuensis* to inhibit β-amyloid production

| fraction (25 μg/ml) | CJ-1 | CJ-2 | CJ-3 | CJ-4 |
|---|---|---|---|---|
| Aβ42 production (%) compared to that of negative control (100%) | 6.6 ± 0.72 | 1.0 ± 0.33 | 1.0 ± 0.46 | 12.3 ± 1.38 |
| Aβ40 production (%) compared to that of negative control (100%) | 53.4 ± 5.01 | 30.7 ± 0.82 | 16.1 ± 1.26 | 47.4 ± 1.36 |

Figure 2:
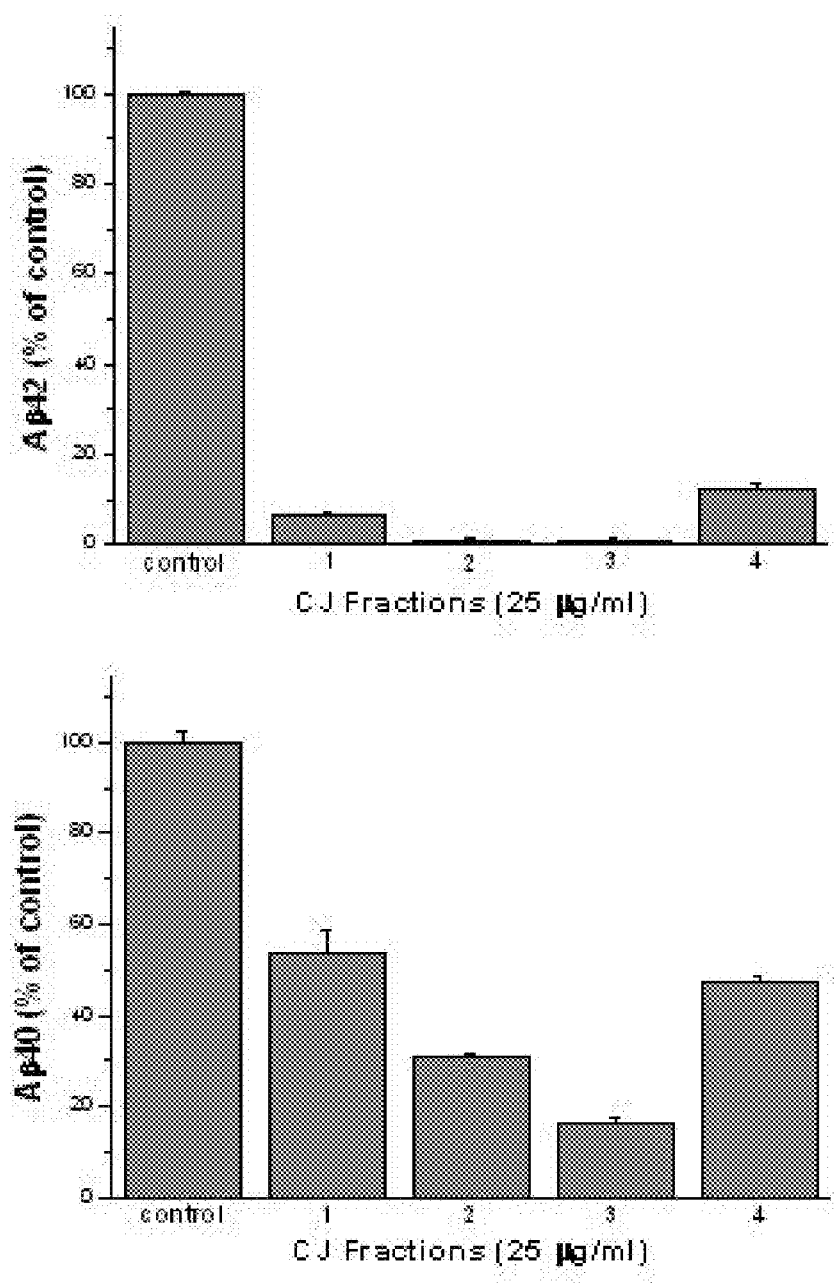
FIG. 2 is a graph showing the effect of *Lycoris chejuensis* fractions (CJ-1, CJ-2, CJ-3, CJ-4) for inhibiting β-amyloid ($A\beta_{40}$, $A\beta_{42}$) production.

From the Table 2 and FIG. 2, it can be seen that β-amyloid (Aβ40, Aβ42) production may be inhibited by all the fractions (CJ-1, CJ-2, CJ-3, CJ-4) of *Lycoris chejuensis*.

Figure 3:
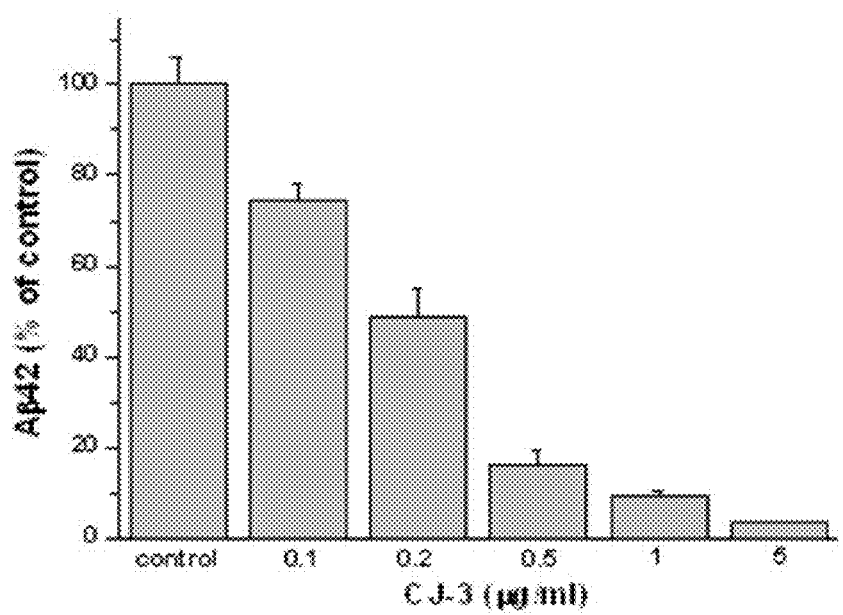
FIG. 3 is a graph showing the effect of butanol fraction of *Lycoris chejuensis* (CJ-3) for inhibiting β-amyloid($A\beta_{42}$) production according to concentration.

In addition, the butanol fraction (CJ-3) of *Lycoris chejuensis* having excellent effect to inhibit β-amyloid (Aβ40, Aβ42) production was added in each concentration of 5, 1, 0.5, 0.2 and 0.1 μg/ml to additionally quantify β-amyloid(Aβ$_{42}$) production. The results are shown in FIG. 3. FIG. 3 shows that β-amyloid(Aβ$_{42}$) production may be inhibited by the butanol fraction (CJ-3) of *Lycoris chejuensis* in a concentration dependent manner.

10 μg/ml of each of the butanol sub-fractions (CJ-3-F1, F2, F3, F4, F5, F6, F7, F8) obtained in Example <1-2> was added by the same procedure as Experimental example <1-1>, and β-amyloid(Aβ$_{42}$) production was quantified. The results are shown in following Table 3 and FIG. 4.

TABLE 3

Effect of sub-fractions of *Lycoris chejuensis* to inhibit β-amyloid production

| | Sub-fraction (10 μg/ml) | | | | | | | |
|---|---|---|---|---|---|---|---|---|
| | CJ-3-F1 | CJ-3-F2 | CJ-3-F3 | CJ-3-F4 | CJ-3-F5 | CJ-3-F6 | CJ-3-F7 | CJ-3-F8 |
| Aβ42 production (%) compared to that of negative control (100%) | 99.9 ± 2.47 | 13.2 ± 2.18 | 5.7 ± 0.44 | 12.1 ± 1.31 | 7.4 ± 1.89 | 9.8 ± 1.02 | 4.7 ± 0.58 | 67.1 ± 0.44 |

Figure 4:
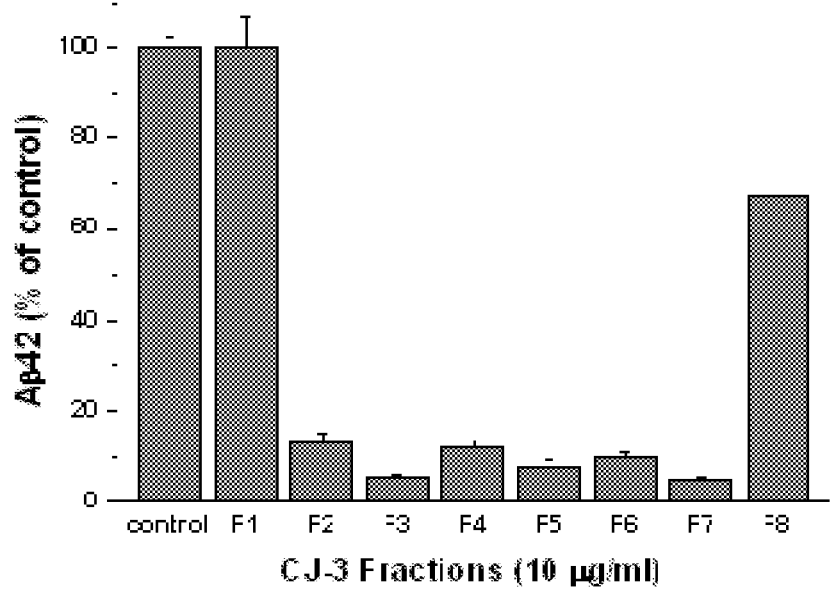
FIG. 4 is a graph showing the effect of butanol sub-fractions of *Lycoris chejuensis* (CJ-3-F1, F2, F3, F4, F5, F6, F7 and F8) for inhibiting β-amyloid ($A\beta_{42}$) production.

From the Table 3 and FIG. 4, it can be seen that β-amyloid (Aβ42) production may be inhibited in the butanol sub-fractions obtained in the <Example 1-2>

Accordingly, it is confirmed that an extract of *Lycoris chejuensis* inhibits β-amyloid(Aβ40, Aβ42) production and thus it may be useful for prevention, improvement and/or treatment of related neurodegenerative diseases, for example, dementia.

Experimental Example 2

Effect of an Extract or a Fraction of *Lycoris Chejuensis* on Cell Death and Safety Evaluation In order to measure the effect of an extraction or a fraction of *Lycoris chejuensis* on cell death, MTT Cell Proliferation assay (ATCC catalog #30-1010K, Manassas, USA), which is a conventionally known method, was used. In particular, a cell was treated with various concentrations of an ethanol extract (CJ) of *Lycoris chejuensis* and a butanol fraction (CJ-3) of *Lycoris chejuensis* for 8 hours, and then, viable cells were quantified. The results are shown in following Table 4, Table 5 and FIG. 5.

TABLE 4

Effect of *Lycoris chejuensis* extract on cell death

| | concentration | | | | | |
|---|---|---|---|---|---|---|
| | 1.0 | 2.5 | 5 | 10 | 25 | 50 |
| Cell viability (%) for CJ (μg/ml) compared to negative control (100%) | 97.6 ± 1.36 | 87.6 ± 1.61 | 90.8 ± 6.84 | 83.9 ± 4.18 | 85.9 ± 2.76 | 65.2 ± 2.66 |

TABLE 5

Effect of *Lycoris chejuensis* fraction on cell death

| | Concentration | | | | |
|---|---|---|---|---|---|
| | 0.1 | 0.2 | 0.5 | 1.0 | 5.0 |
| Cell viability (%) for CJ-3 (μg/ml) compared to negative control (100%) | 107.6 ± 1.71 | 106.2 ± 4.53 | 107.4 ± 2.43 | 99.1 ± 7.08 | 81.6 ± 5.21 |

Figure 5:
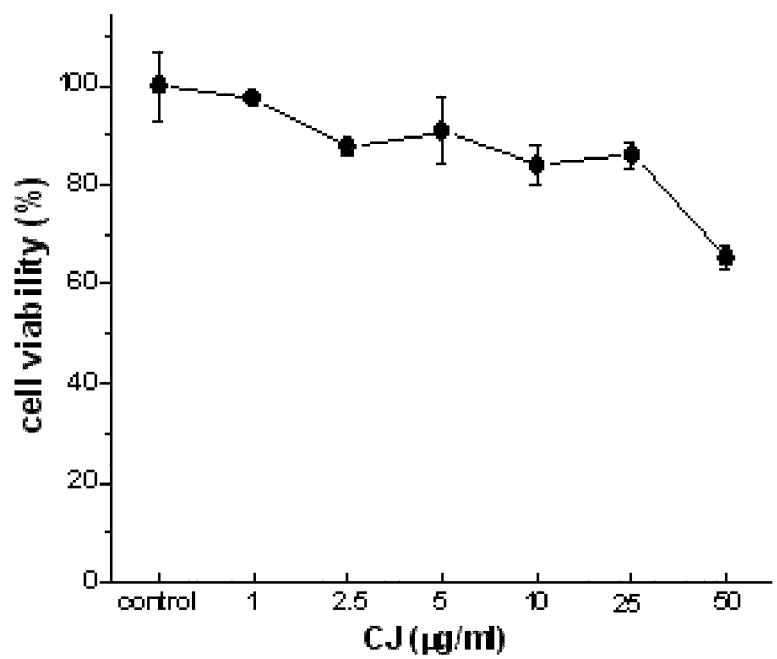
FIG. 5 is a graph showing the effect of an ethanol extract (CJ) or a butanol fraction (CJ-3) on cell death.
Figure 5:
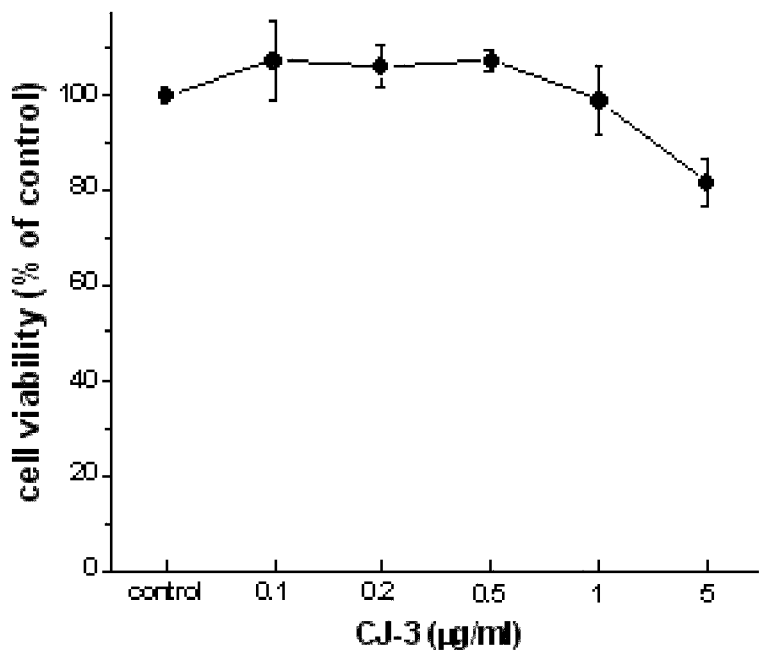

From the Table 4, Table 5 and FIG. 5, it can be seen that when the ethanol extract (CJ) of *Lycoris chejuensis* was administered in concentration of 50 μg/ml, cells of only 30% or less died, and when the butanol fraction (CJ-3) of *Lycoris chejuensis* was administered in concentration of 5 μg/ml, cells of only 20% or less died.

Accordingly, it is confirmed that the inhibition of *Lycoris chejuensis* extracts and fractions for β-amyloid($A\beta_{40}$, $A\beta_{42}$) production is not simply due to cell death, and that the extract of *Lycoris chejuensis* has weak cell toxicity and it may be safely used for a living body, even if it administered in large amount.

Experimental Example 3

Figure 6:
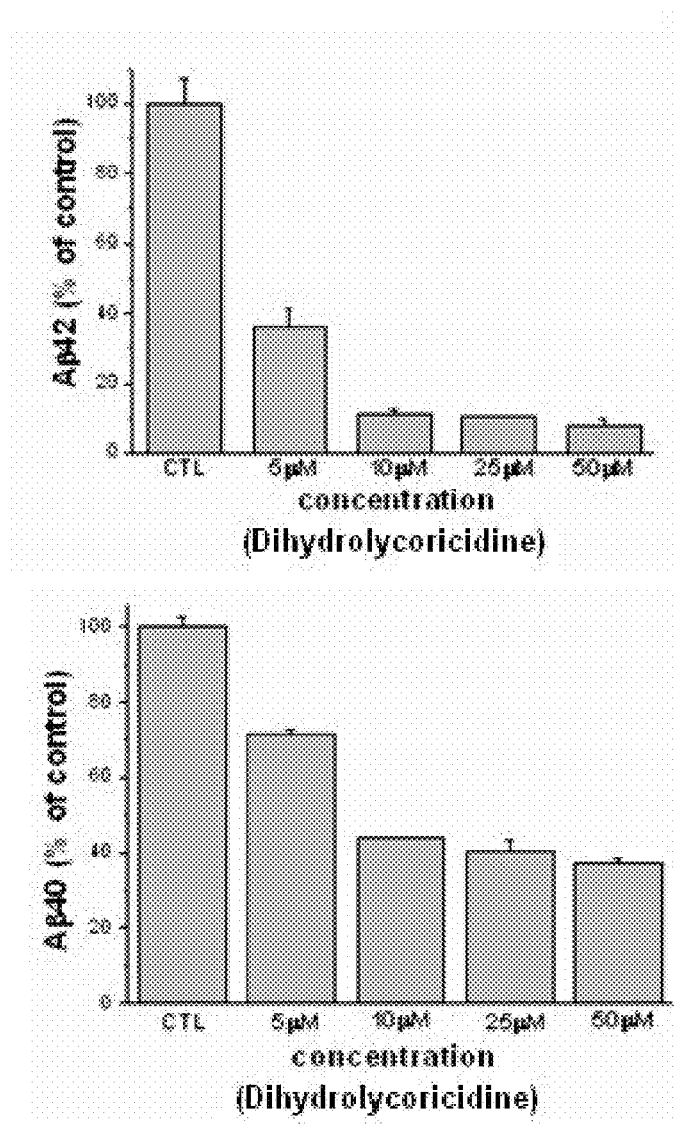
FIG. 6 is a graph showing the effect of dihydrolycoricidine for inhibiting β-amyloid ($A\beta_{40}$, $A\beta_{42}$) production according to concentration (CTL: negative control).

Effect of the Compounds of the Invention for Inhibiting β-amyloid Production 3-1 Effect of Dihydrolycoricidine for Inhibiting β-amyloid Production In order to examine the effect of dihydrolycoricidine obtained in Example <2-1> to inhibit β-amyloid production, β-amyloid production upon the addition of dihydrolycoricidine was quantified by the same procedure as Experimental example <1-1>, and the results are shown in following Table 6 and FIG. 6. The negative control means the case to which Dihydrolycoricidine was not added.

TABLE 6

Effect of dihydrolycoricidine to inhibit β-amyloid production

| | Concentration of the compound of the present invention(μM) | | | |
|---|---|---|---|---|
| | 50 | 25 | 10 | 5 |
| Inhibition rate (%) of Aβ40 production compared to that of negative control | 63.0 | 59.8 | 56.1 | 28.4 |
| Inhibition rate (%) of Aβ42 production compared to that of negative control | 92.2 | 88.8 | 63.8 | 58.8 |

The above Table 6 and FIG. 6 show that β-amyloid($A\beta_{40}$, Aβ42) production may be inhibited by dihydrolycoricidine in a concentration dependent manner.

3-2 Effect of 2-Methoxypancracine to Inhibit β-amyloid Production

Figure 7:
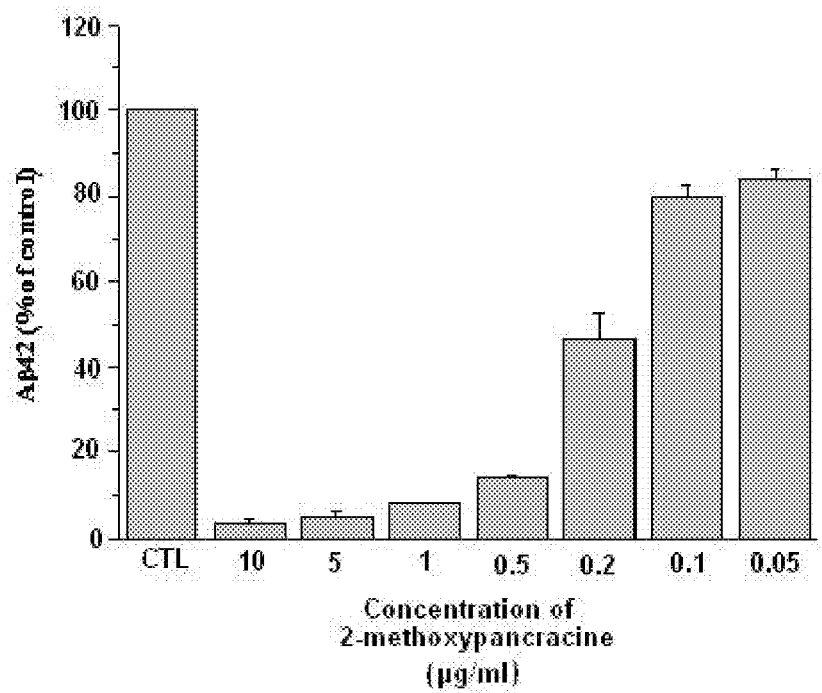
FIG. 7 is a graph showing the effect of 2-methoxypancracine for inhibiting β-amyloid ($A\beta_{40}$, $A\beta_{42}$) production according to concentration (CTL: negative control).
Figure 7:
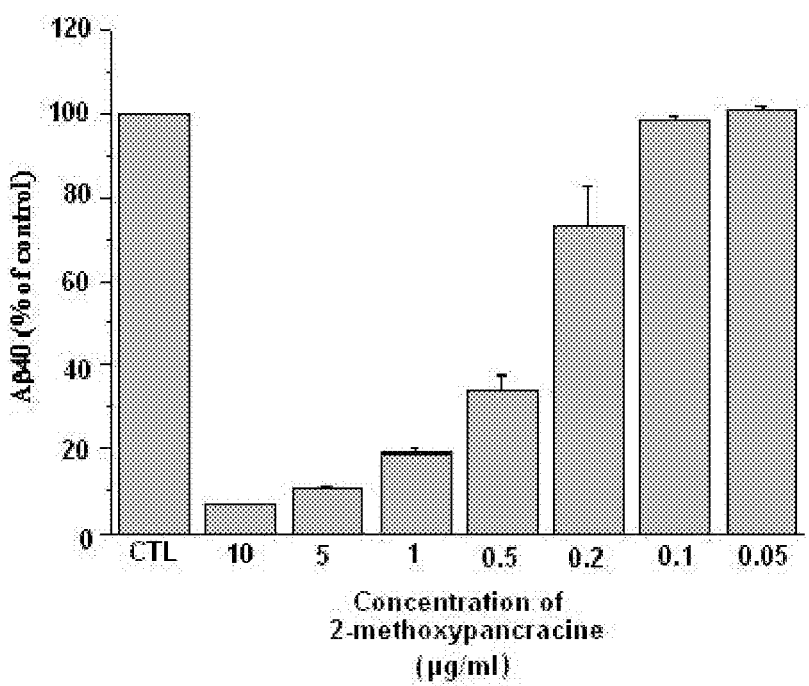

In order to examine the effect of 2-methoxypancracine obtained in Example <2-2> to inhibit β-amyloid production, β-amyloid production upon the addition of 2-methoxypancracine was quantified by the same method as Experimental example <1-1>. In particular, each of 10, 5, 1, 0.5, 0.2, 0.1, and 0.05 μg/ml of 2-methoxypancracine was added and cultured for 8 hours, and then, the culture fluids were recovered, and β-amyloid production was quantified by the same procedure as Experimental example <1-1>. The results are shown in FIG. 7. The negative control means the case to which 2-methoxypancracine was not added. FIG. 7 shows that β-amyloid($A\beta_{40}$, Aβ42) production may be inhibited by 2-methoxypancracine in a concentration dependent manner.

3-3 Effect of Lycoricidine to Inhibit β-amyloid Production

In order to examine the effect of lycoricidine obtained in Example <2-1> to inhibit β-amyloid production, β-amyloid production upon the addition of lycoricidine was quantified by the same procedure as Experimental example <1-1>. In particular, each of 10, 1, 0.1, and 0.01 μg/ml of lycoricidine was added and cultured for 8 hours, and then, the culture fluids were recovered, and β-amyloid production was quantified by the same procedure as Experimental example <1-1>. The results are shown in following Table 7, and FIGS. 8*a* and 8*b*. The negative control means the case to which lycoricidine was not added.

TABLE 7

Effect of lycoricidine to inhibit β-amyloid production

| | lycoricidine | | | |
|---|---|---|---|---|
| Concentration (μg/ml) | 0.01 | 0.1 | 1 | 10 |
| Inhibition rate (%) of Aβ42 production compared to that of negative control | 16.0 | 81.3 | 97.5 | 100 |
| Inhibition rate (%) of Aβ40 production compared to that of negative control | 3.3 | 67.0 | 92.8 | 97.2 |

Figure 8A:
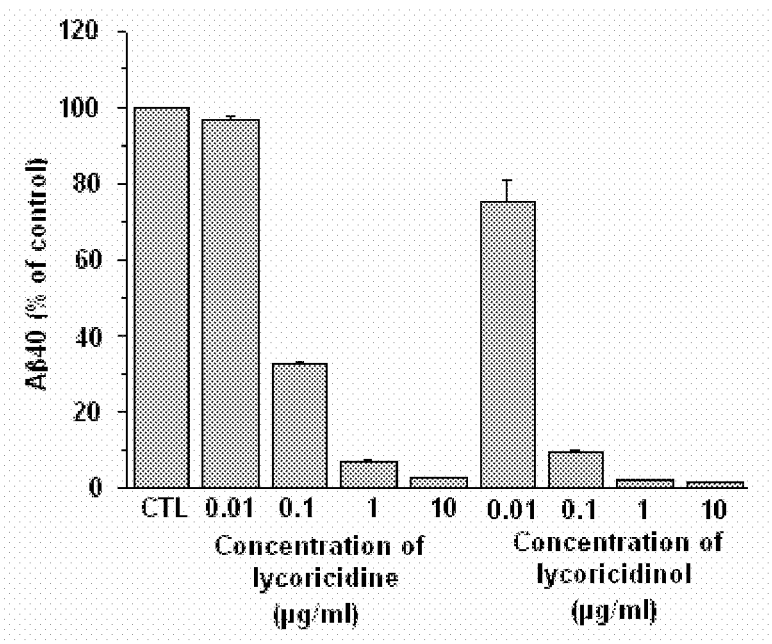
FIGS. 8a and 8b are graphs showing the effects of lycoricidine and lycoricidinol for inhibiting β-amyloid ($A\beta_{40}$: 8a; $A\beta_{42}$: 8b) production according to concentration (CTL: negative control).
Figure 8B:
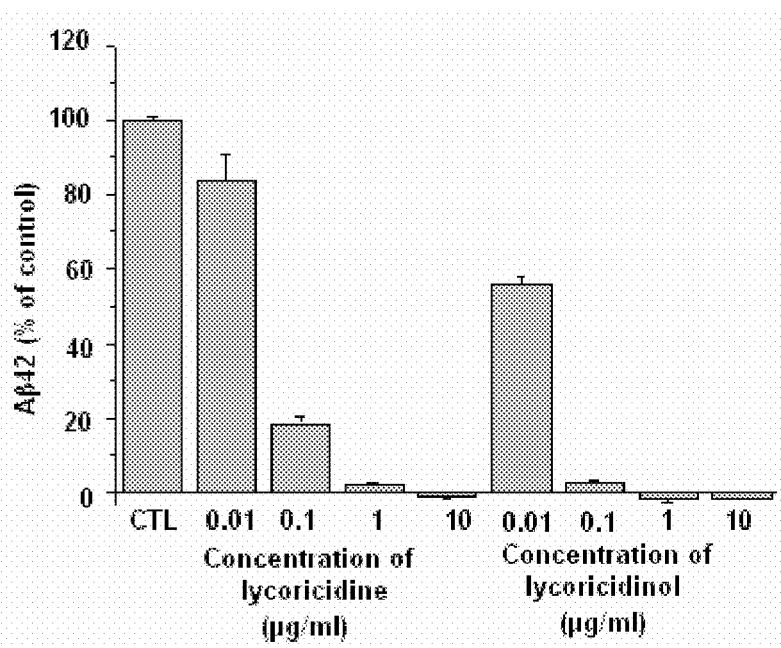

The above Table 7 and FIGS. 8*a* and 8*b* show that β-amyloid($A\beta_{40}$, Aβ42) production may be inhibited by lycoricidine in a concentration dependent manner.

3-4 Effect of Lycoricidinol to Inhibit β-amyloid Production

In order to examine the effect of lycoricidinol obtained in Example <2-2> to inhibit β-amyloid production, β-amyloid production upon the addition of lycoricidinol was quantified by the same procedure as Experimental example <1-1>. In particular, each of 10, 1, 0.1, and 0.01 μg/ml of lycoricidinol was added and cultured for 8 hours, and then, the culture fluids were recovered, and β-amyloid production was quantified by the same procedure as Experimental example <1-1>. The results are shown in following Table 8, and FIGS. 8*a* and 8*b*. The negative control means the case to which lycoricidine was not added.

TABLE 8

Effect of lycoricidinol to inhibit β-amyloid production

|  | lycoricidinol | | | |
| --- | --- | --- | --- | --- |
| Concentration (μg/ml) | 0.01 | 0.1 | 1 | 10 |
| Inhibition rate (%) of Aβ42 production compared to that of negative control | 44.0 | 97.0 | 100 | 100 |
| Inhibition rate (%) of Aβ40 production compared to that of negative control | 25.0 | 90.4 | 97.8 | 98.4 |

The above Table 8 and FIGS. 8a and 8b show that β-amyloid(Aβ$_{40}$, Aβ42) production may be inhibited by lycoricidinol in a concentration dependent manner.

Experimental Example 4

Effect of the Compounds of the Invention to Inhibit the Production of β-secretase Product(sAPPβ)

The cause of inhibition of β-amyloid production in the Experimental example <3> was examined in more detail. β-amyloid was produced from amyloid precursor(APP) by continuous actions of membrane protein hydrolytic enzyme, β-secretase (BACE1), and γ-secretase (Vassa and Citron, Neuron 27, 419-422, 2000). More specifically, β-secretase product(sAPPβ) is produced from amyloid precursor (APP) by the action of β-secretase, from which β-amyloid is produced by the action of γ-secretase.

Based on the above, it was identified whether or not dihydrolycoricidine obtained in Example <2-1> is capable of inhibiting the production of β-secretase product(sAPPβ). Specifically, the same procedure as Experimental example <3> was conducted except that sAPPβ-Wild Type Assay Kit (Immuno-Biological Laboratories Co., Ltd., Japan) was used for quantifying sAPPβ. The results are shown in Table 9 and FIG. 9. The negative control means the case to which dihydrolycoricidine was not added.

TABLE 9

Effect of dihydrolycoricidine to inhibiting sAPPβ production

|  | Concentration of the compound of the present invention(μM) | | | |
| --- | --- | --- | --- | --- |
|  | 50 | 25 | 10 | 5 |
| Inhibition rate (%) of sAPPβ production compared to negative control | 36.1 | 28.9 | 12.0 | 6.0 |

Figure 9:
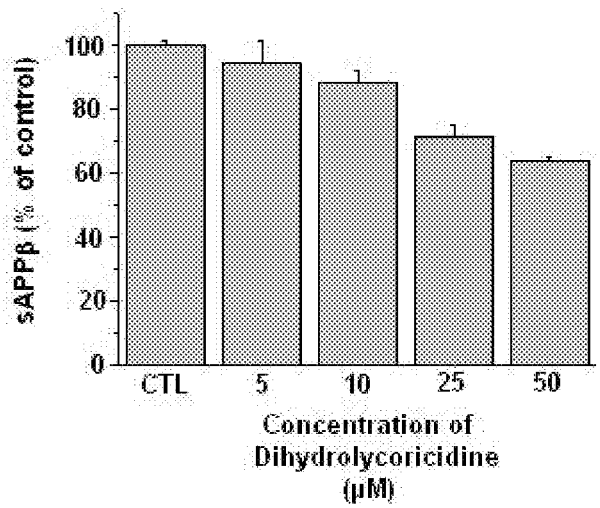
FIG. 9 is a graph showing the effect of dihydrolycoricidine for inhibiting the production of β-secretase product (sAPPβ) according to concentration (CTL: negative control).

The above Table 9 and FIG. 9 show that the production of β-secretase product(sAPPβ) may be inhibited by dihydrolycoricidine. Thus, it can be seen that dihydrolycoricidine inhibits the activity of β-secretase to decrease sAPPβ production, thereby inhibiting β-amyloid production.

Experimental 5

Effect of the Compound of the Invention on Cell Death and Safety Evaluation 5-1 Dihydrolycoricidine In order to evaluate the effect of dihydrolycoricidine obtained in Example <2-1> on cell death, viable cells were quantified by the same procedure as the Experimental example <2> and the results are shown in the following Table 10 and FIG. 10.

TABLE 10

Effect of dihydrolycoricidine on cell death

|  | Concentration of the compound of the present invention(μM) | | | |
| --- | --- | --- | --- | --- |
|  | 5 | 10 | 25 | 50 |
| Cell death (%) compared to negative control | 18.3 | 23.3 | 25.3 | 28.1 |

Figure 10:
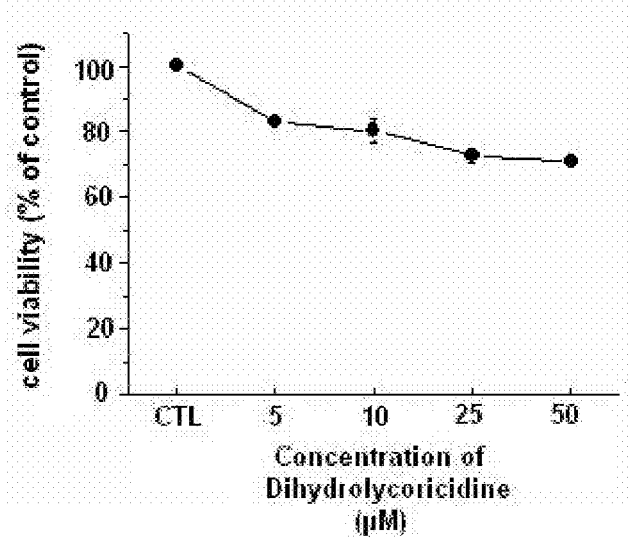
FIG. 10 is a graph showing the effect of dihydrolycoricidine on cell death according to concentration (CTL: negative control).

As shown in the above Table 10 and FIG. 10, when the compound of the present invention was administered in concentration of 50 μM, cells of only 30% or less died. Thus, it can be seen that the inhibition effect of dihydrolycoricidine for β-amyloid production is not simply due to cell death, and that dihydrolycoricidine has weak cell toxicity, even if it is administered in large amount, and thus it can be safely used for a living body as an active gradient in a pharmaceutical or food composition.

5-2 2-Methoxypancracine

Figure 11:
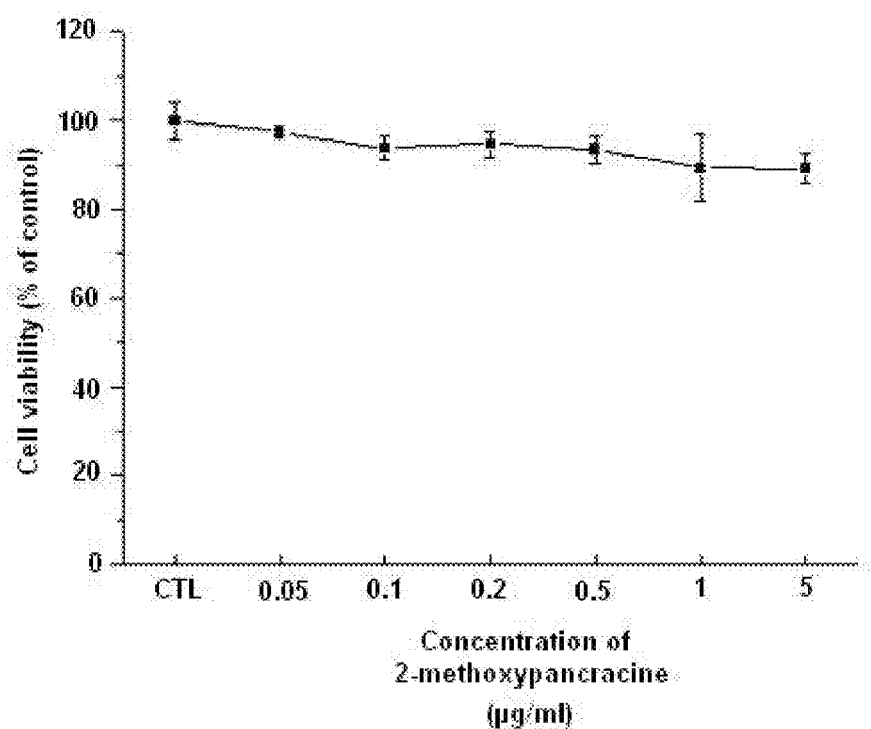
FIG. 11 is a graph showing the effect of 2-methoxypancracine on cell death according to concentration (CTL: negative control).

In order to evaluate the effect of 2-methoxypancracine obtained in Example <2-2> on cell death, viable cells were quantified by the same procedure as Experimental example <2> and the results are shown in FIG. 11.

As shown in FIG. 11, when 2-methoxypancracine was administered in concentration of 5 μg/ml, cells of only 10% or less died. Thus, it can be seen that the inhibition of 2-methoxypancracine for β-amyloid production is not simply due to cell death, and that 2-methoxypancracine has weak cell toxicity, even if it is administered in large amount, and thus it can be safely used for a living body as an active gradient in a pharmaceutical or food composition.

5-3 Lycoricidine

In order to evaluate the effect of lycoricidine obtained in Example <2-1> on cell death, viable cells were quantified by the same procedure as the Experimental example <2> and the results are shown in the following Table 11 and FIG. 12.

TABLE 11

Effect of lycoricidine on cell death

|  | lycoricidine | | | |
| --- | --- | --- | --- | --- |
| Concentration (μg/ml) | 0.01 | 0.1 | 1 | 10 |
| Cell death (%) compared to negative control | 4.9 | 11.3 | 19.0 | 21.1 |

Figure 12:
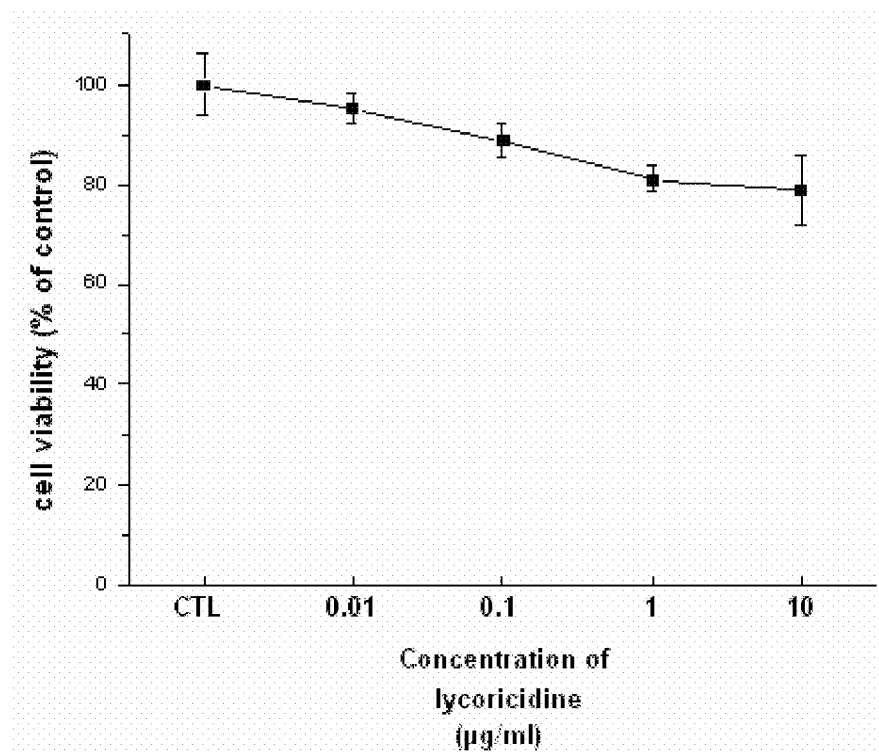
FIG. 12 is a graph showing the effect of lycoricidine on cell death according to concentration (CTL: negative control).

As shown in the above Table 11 and FIG. 12, when the compound of the present invention was administered in concentration of 10 μM, cells of only 20% or less died. Thus, it can be seen that the inhibition effect of lycoricidine for β-amyloid production is not simply due to cell death, and that lycoricidine has weak cell toxicity, even if it is administered in large amount, and thus it can be safely used for a living body as an active gradient in a pharmaceutical or food composition.

5-4 Lycoricidinol

Figure 13:
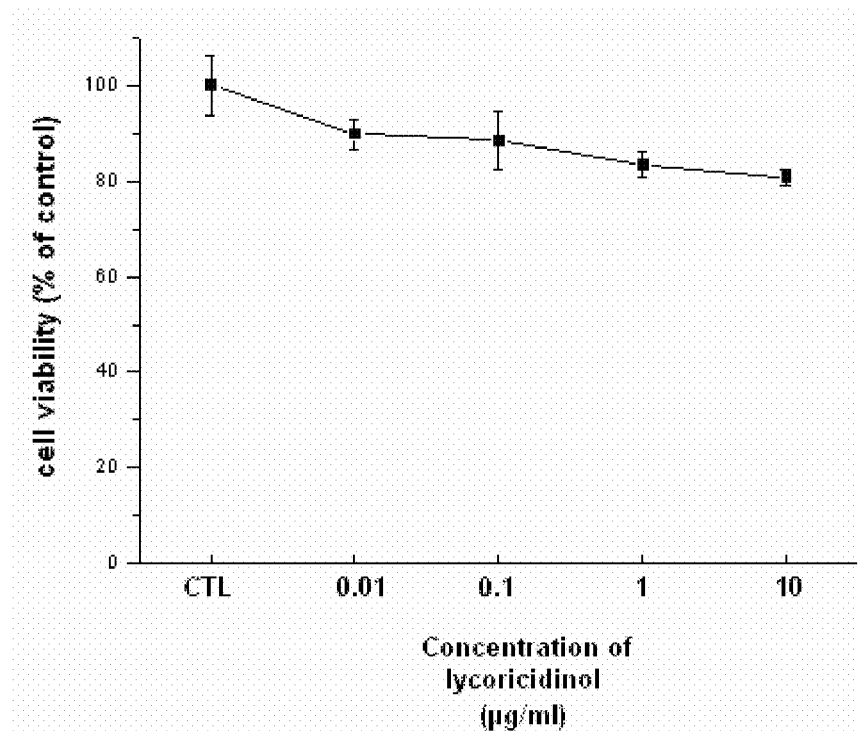
FIG. 13 is a graph showing the effect of lycoricidinol on cell death according to concentration (CTL: negative control).

In order to evaluate the effect of lycoricidinol obtained in Example <2-2> on cell death, viable cells were quantified by the same procedure as Experimental example <2> and the results are shown in Table 12 and FIG. 13.

TABLE 12

Effect of lycoricidinol on cell death

| | lycoricidinol | | | |
|---|---|---|---|---|
| Concentration (μg/ml) | 0.01 | 0.1 | 1 | 10 |
| Cell death (%) compared to negative control | 10.3 | 11.6 | 16.5 | 19.3 |

As shown in the above Table 12 and FIG. 13, when the compound of the present invention was administered in concentration of 10 μM, cells of only 20% or less died. Thus, it can be seen that the inhibition effect of lycoricidinol for β-amyloid production is not simply due to cell death, and that lycoricidinol has weak cell toxicity, even if it is administered in large amount, and thus it can be safely used for a living body as an active gradient in a pharmaceutical or food composition.

As explained, an extract of *Lycoris chejuensis* may effectively inhibit production of β-amyloid which is known to be a causative material of dementia, particularly Alzheimer's disease, and thus a composition containing the same as an active ingredient may be useful for prevention or treatment of a neurodegenerative disease, such as dementia. In addition, the compounds of the present invention may inhibit production of β-amyloid which is known to be causative material of dementia, particularly Alzheimer's disease, and production of β-secretase product(sAPPβ), and thus a composition containing the same as an active ingredient may be useful for prevention or treatment of a neurodegenerative disease, such as dementia.

What is claimed is:

1. A method of treating a neurodegenerative disease comprising administering an extract of *Lycoris chejuensis* to a patient in need of treatment of a neurodegenerative disease, wherein the neurodegenerative disease is caused by $A\beta_{42}$ production;
   wherein the extract comprises lycoricidine as an active ingredient; and
   wherein the extract of *Lycoris chejuensis* is obtained by extracting *Lycoris chejuensis* with one or more solvents selected from the group consisting of water and $C_1$ to $C_4$ lower alcohol.

2. The method according to claim 1, wherein the neurodegenerative disease is selected from the group consisting of dementia, Parkinson's disease, Alzheimer's disease, Huntington's disease, Pick's Disease, and Parkinson's disease-ALS(amyotrophic lateral sclerosis)-dementia complex.

3. The method according to claim 1, further comprising extracting the extract obtained according to claim 1 with one or more solvents selected from the group consisting of water, hexane, methylene chloride, ethyl acetate, and $C_1$ to $C_4$ lower alcohol.

4. The method according to claim 3, further comprising extracting the extract obtained according to claim 3 with one or more solvents selected from the group consisting of acetonitrile, $C_1$ to $C_4$ lower alcohol, acetone, and water.

5. A method of inhibiting β-amyloid production comprising administering an extract of *Lycoris chejuensis* to a patient in need of inhibition of β-amyloid production,
   wherein the extract comprises lycoricidine as an active ingredient; and
   wherein the extract of *Lycoris chejuensis* is obtained by extracting *Lycoris chejuensis* with one or more solvents selected from the group consisting of water and $C_1$ to $C_4$ lower alcohol.

6. The method according to claim 5, further comprising extracting the extract obtained according to claim 5 with one or more solvents selected from the group consisting of water, hexane, methylene chloride, ethyl acetate, and $C_1$ to $C_4$ lower alcohol.

7. The method according to claim 6, further comprising extracting the extract obtained according to claim 6 with one or more solvents selected from the group consisting of acetonitrile, $C_1$ to $C_4$ lower alcohol, acetone, and water.

* * * * *